United States Patent [19]

Molnar

[11] 3,956,489

[45] May 11, 1976

[54] CERTAIN MIXED ANTIBACTERIALS

[76] Inventor: Nicholas M. Molnar, New York, N.Y.

[22] Filed: Jan. 23, 1974

[21] Appl. No.: 435,896

Related U.S. Application Data

[63] Continuation-in-part of Ser. No. 242,763, April 10, 1972, abandoned.

[52] U.S. Cl.............................. 424/233; 424/235; 424/329; 424/341; 424/347; 252/107
[51] Int. Cl.............................................. A01n 9/02
[58] Field of Search ............ 424/233, 235, 329, 341

[56] References Cited
UNITED STATES PATENTS
3,652,764   3/1972   Lamberti et al. .................... 424/346

Primary Examiner—V. D. Turner
Attorney, Agent, or Firm—Jacobs & Jacobs

[57] ABSTRACT

Aqueous antibacterial compositions for use as surgical scrubs, antiseptic skin cleansers and hand lotions are prepared from a combination of (a) at least one halogenated salicylanilide, carbanilide or thiocarbanilide; (b) at least one halogenated diphenylhydroxy ether or bisphenol; and (c) a quaternary salt derived from an ethoxylated or propoxylated polyol. The compositions are of low toxicity and possess an extremely high order of activity against both Gram-positive and Gram-negative organisms.

8 Claims, No Drawings

CERTAIN MIXED ANTIBACTERIALS

CROSS REFERENCE TO RELATED APPLICATION

This is a continuation-in-part of my copending application Ser. No. 242,763, filed Apr. 10, 1972, entitled "Antibacterial Compositions," now abandoned, which is incorporated herein by reference.

DETAILED DESCRIPTION

It is well known that various aromatic ring halogenated compounds possess marked antimicrobial activity. Such substances include ring halogenated salicylanilides, halogenated carbanilides and halogenated thiocarbanilides. It is also known that the utility of these substances and in particular their ease of formulation is in many instances hindered by low solubility in aqueous media. Various solutions to this problem have been found, as for example, the utilization of certain quaternary salts as solubilizing agents; see e.g. British specification Nos. 1,161,671 and 1,161,672. Certain quaternary ammonium compounds themselves have excellent antimicrobial activity, but surprisingly the combination of an aromatic ring halogenated compound and antibacterial quaternary salt produces results which are no more than additive and often less than additive. One possible explanation for this phenomenon is the orientation of the quaternary salt when absorbed as a film on the bacteria. Thus, whereas benzalkonium chloride ordinarily kills bacteria, dried bacteria which are coated with a greasy film can survive many hours of contact with this quaternary salt, presumably because of its absorption being oriented with the harmless hydrocarbon moiety in contact with the bacteria; see Rahm, Proc. Soc. Exptl. Biol. Med., 62, 2–4 (1946). Fatty material also seems to protect Staphylococcus aureus against cetyl pyridinium chloride. Cationic soaps are also known to form films which are very resistant to mechanical removal from the skin, with the inner surface of the film showing low bactericidal activity and the outerside of the film strong bactericidal activity. The formation of such films will of course have little effect on combating bacteria if the bacteria remains underneath. See Miller et al, Proc. Soc. Exptl. Biol. Med. 54, 174–6 (1943).

The present invention is based upon the discovery that a combination of two antibacterial agents together with a solubilizing quaternary salt, which itself demonstrates antibacterial activity, results in a degree of antibacterial activity which, in most cases, greatly exceeds the additive effects of the individual components. As will be seen hereafter, this overall effect appears to be largely dependent upon the presence of all three components since the activity of any two of the threee components corresponds to that previously observed, i.e. additive effects. Under the most ideal conditions, the bacteriostatic activity of 3,4',5-tribromo salicylanilide alone against Pseudomonas aeruginosa is 75 ppm. The incorporation of 2% soap reduces this activity to 160 ppm, based on active ingredient. The minimum inhibitory concentration of 2,4,4'-trichloro-2'-hydroxydiphenyl ether alone against Pseudomonas aeruginosa is reported to be greater than 300 ppm. In the presence of a surfactant such as soap, no practical activity is demonstrable. By contrast, the composition of the present invention has anti-bacterial activity even in the presence of a surfactant.

The present invention employs as a first component of the composition an antibacterially effective amount of at least one halogenated salicylanilide, carbanilide or thiocarbanilide having one or two halogen atoms on each phenyl ring and up to one trifluoromethyl on one phenyl ring. Preferably, the halogen atom is chlorine or bromine. These materials are well known to the art and include such species as 3,4',5-tribromo salicylanilide, 3,5-dibromo salicylanilide, 4',5-dibromo salicylanilide, 5-chloro-2',4'-dibromo salicylanilide, 3,4',5-trichloro salicylanilide, 4'-chloro-5-bromo salicylanilide, 2',3,4',5-tetrabromo salicylanilide, 3,4,4'-trichlorocarbanilide and 3-trifluoromethyl-4,4'-dichloro carbanilide. Other suitable compounds of this type are disclosed for example in J. Pharmaceutical Sciences, 50, No. 10,831–837 (1961) and in Arzneimittel Forschung, 4, Heft. 9, 1954. Preferred species of this class as 3,4',5-trichloro salicylanilide, 3,4,4'-trichloro carbanilide, 3-trifluoromethyl-4,4'-dichloro carbanilide and in particular 3,4',5-tribromo salicylanilide and 2',3,4',5-tetrabromo salicylanilide.

The second component of the present composition comprises at least one halogenated 2-hydroxydiphenyl ether or bisphenol.

It is preferred to use a halogenated 2-hydroxydiphenyl ether having one or two halogen atoms on each phenyl ring. Preferably, the halogen atoms are chlorine or bromine. Such halogenated 2-hydroxydiphenyl ethers are well known and described in greater detail in, for example, U.S. Pat. No. 3,506,720. Preferred species of this class include 2,4,4'-trichloro-2'-hydroxydiphenyl ether and 4,4'-dichloro-2'-hydroxydiphenyl ether.

The halogenated bisphenol has the formula

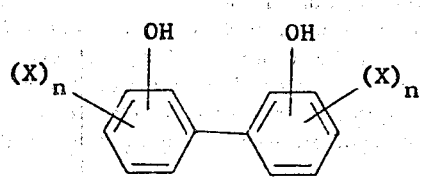

where X is halogen, preferably chlorine or bromine and where n is 1–4, preferably 1 or 2. These compounds may be prepared by brominating bisphenol under normal conditions, such as atmospheric pressure and a temperature below 100°C, to introduce one or two bromine atoms per phenyl ring. To introduce more than two bromine atoms per phenyl ring, it is necessary to use a Friedel Crafts catalyst, such as aluminum chloride or iron bromide in an anhydrous medium. See, for example, Berichte, 35, p.303, 1902. Typical compounds of this class are 3,3'-dibromo-2,2'-biphenyldiol, 3,3',5,5'-tetrabromo-2,2'-biphenyldiol, 3,3',5,5'-tetrabromo-4,4'-biphenyldiol, octachloro-2,2'-biphenyldiol, 2,2',6,6'-tetrabromo-3,3'-biphenyldiol, and 2,2',6,6'-tetrabromo-4,4'-biphenyldiol.

The quaternary salt of the present invention can be diagrammatically depicted as having the formula (I) below:

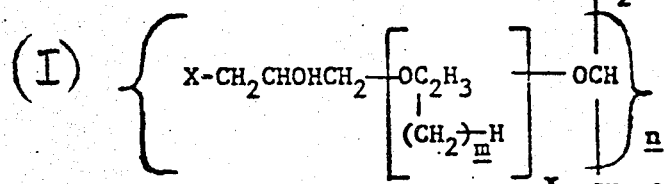
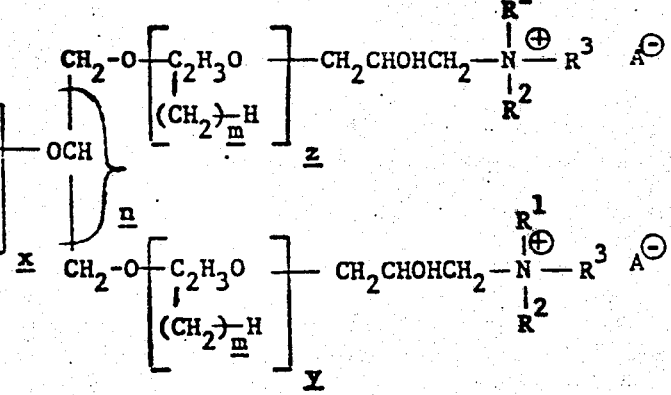

wherein
X is chlorine or bromine;
each of $R^1$ and $R^2$ is alkyl of 1 to 3 carbon atoms;
$R^3$ is alkyl, alkenyl or haloalkyl of 6 to 18 carbon atoms;
$A^-$ is a physiological acceptable monovalent anion;
each of $x$, $y$ and $z$, independent of the other, has a value of from 1 to 10;
the sum of $x$, $y$ and $z$ is 9 to 15;
$m$ has a value of 0 or 1; and
$n$ has a value of from 1 to 4.

Quaternary salts of this type are disclosed in my co-pending application Ser. No. 223,308 filed Feb. 3, 1972 entitled "Antibacterial Quaternary Ammonium Salts and Method of Preparing Same," which is incorporated herein by reference. In particular, preferred quaternary salts are those in which X is chloro, $A^-$ is the chloride anion, $m$ is 0, $n$ is 1, the sum of $x$, $y$ and $z$ is approximately 12, $R^1$ and $R^2$ are both methyl, and $R^3$ is a mixture of hydrocarbon chains, 65% dodecyl, 25% tetradecyl and 10% hexadecyl. This quaternary salt is commercially available from Fine Organics, Inc. under the designation HQ8.

The backbone of the novel quaternary salts is formed by a polyol of the formula $HOCH_2-(CHOH)_n-CH_2OH$, where $n$ is 1 to 4. Illustrative of this group are glycerol, erythritol and sorbitol. The polyol is condensed with an appropriate 1,2-epoxyalkane of the formula

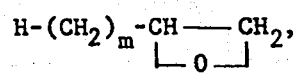

where $m$ is as defined above, such as ethylene or propylene oxide. The resulting polyether of the formula:

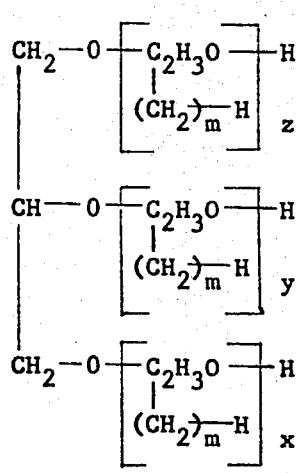

where $m$ and $x$, $y$ and $z$ are as defined above, is next reacted with epichloro or epibromohydrin. Finally, the obtained organic halide of the formula:

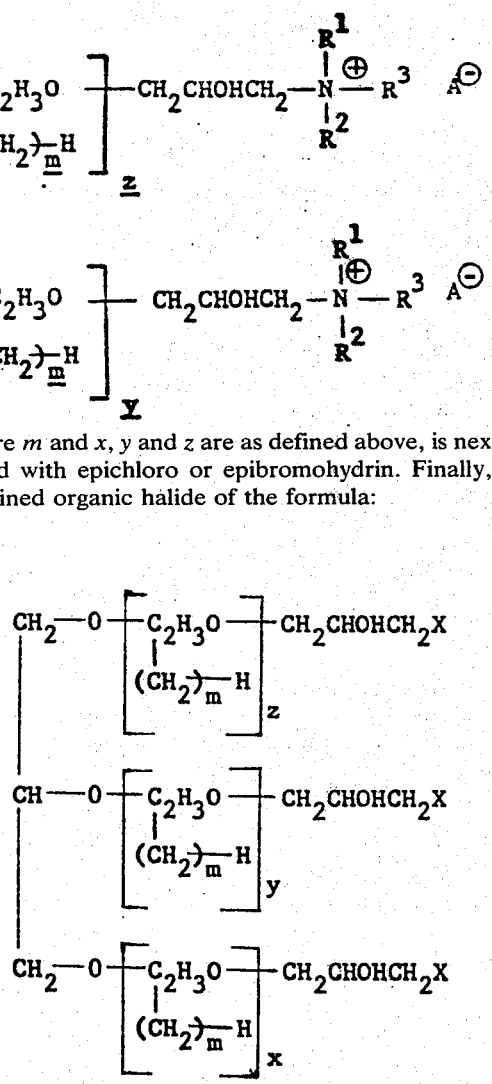

where $m$, $x$, $y$, $z$ and X are as defined above, is condensed with a tertiary amine of the formula $NR^1R^2R^3$, where $R^1$, $R^2$ and $R^3$ are as defined above to form the quaternary salt of formula I. Illustrative examples of the tertiary amine are decyl dimethylamine, dodecyl dimethylamine and di-n-propyl octylamine. In connection with the latter reaction, the unexpected observation was made that only the two halides whose positions correspond to the position of the primary alcoholic groups in the starting polyol react with the tertiary amine employed. The following illustrates the sequence of reactions and the chemical operations involved.

A. The intermediate product (II) is prepared from commercially available ethoxylated glycerol as follows:

To 648g (1 mol) of ethoxylated glycerin (containing approximately 12 ethylene groups) and 3 milliliters of the $BF_3$-ether complex add 278g of epichlorohydrin at 90°C, then cool to 25°C; add 21 grams of active $Al_2O_3$ followed by 600 ml of acetone; filter off $Al_2O_3$ and strip acetone.

The immediate product (II) is a viscous liquid. Yield: 877g. Equivalent weight of intermediate (II) is 309 (one-third of mol. wt.).

The reaction may be illustrated by the following equation:

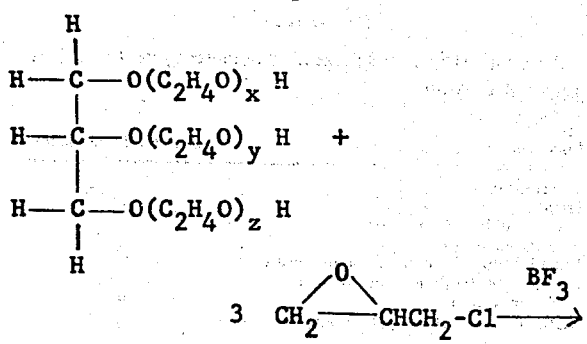

(Intermediate II)

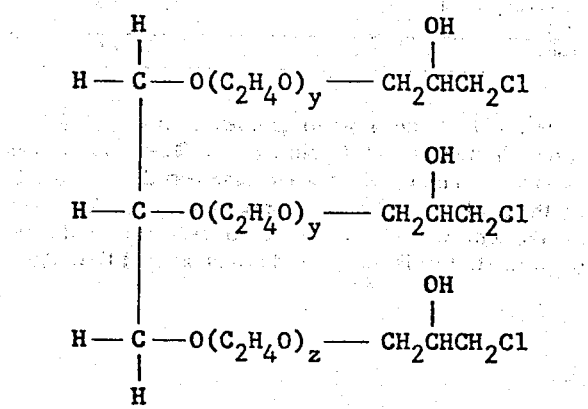

$x + y + z$ = approximately 12

B. Mix 309g (1/3 mol) of (II)
180.5g (2/3 mol) dimethyl dodecylamine and 600 ml n-butanol.

Maintain the reaction mixture at 115°–120°C for 18 hours. Then strip off butanol; a viscous fluid containing the quaternary salt is obtained in nearly quantitative yield. The quaternary salt thus formed has the formula:

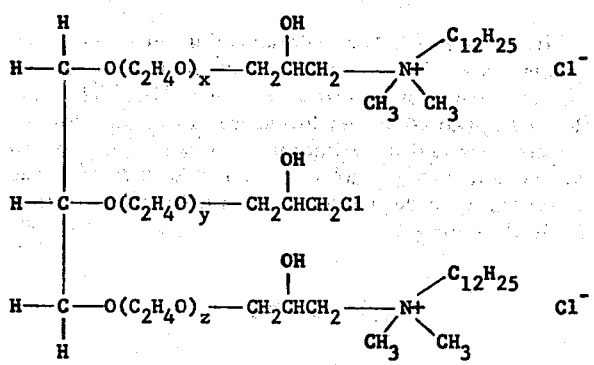

where the sum of $x$, $y$ and $z$ is approximately 12.

While dodecylamine is used in this illustrative preparation, any $C_6$–$C_{18}$ amine, or mixture thereof, can be used, such as a commercial trialkylamine containing, for instance, 65% $C_{12}$, 25% $C_{14}$ and 10% $C_{16}$ alkyl groups. Likewise, any other suitable tertiary base may be used as the quaternizing agent, such as one containing higher alkenyl or halogen-substituted alkyl or alkenyl groups, and in place of the methyl groups, one may be ethyl or propyl or both ethyl and propyl.

The amount of each of the three components in the composition of the present invention is that which will produce in combination with the other ingredients an increased antibacterial effect, as may be readily determined through well known and simple tests such as determination of the minimum inhibitory concentration. In the case of the halogenated salicylanilide, carbanilide or thiocarbanilide, this amount is generally from about 0.05% to about 3% by weight of the composition. The halogenated 2-hydroxydiphenyl ether or bisphenol is in turn present in an amount of from about 0.025% to about 1% of the total weight of the composition. Finally the quaternary salt is generally employed in amounts ranging from about 0.2% to about 4% of the total weight of the composition.

As noted above, the final composition is in the form of an aqueous solution or suspension and thus, in addition to water, the composition may include additional components such as foam builders, cleansing agents, viscosity building agent, hydrotropes, coupling agents, buffering agents, stabilizers and the like. The selection of these adjuvants is determined according to the usual considerations of mutual compatibility, activity, stability and physiological acceptability such as lack of irritation.

Generally the final solution should have a pH of about 7.5 to about 10, preferably 8 to 9, in order to provide good sudsing and cleansing action while maintaining the underlying antibacterial activity. This pH is below that of normal soap and upon dilution with 5 volumes of water, the final pH will generally be from about neutrality to about 9.5. Maintenance of the desired pH can be obtained through the use of buffering agents, as for example borax. Other ingredients which may be added include monoesters of sodium sulfosuccinate, alkanolamine condensate and triethanolamine lauryl sulfates as detergents and foaming agents, xylene sodium sulfonate, a stabilizing agent producing a clear, stable product, propylene glycol, a coupling agent which also imparts stability to the product and the like.

As noted above, the compositions of the present invention find use as surgical scrubs, antiseptic skin cleansers, disinfectants and the like. The compositions not only effect a reduction in bacteria count on the skin but also form a residual antimicrobial mantle. In addition to their antibacterial activity, the compositions have a sudsing and cleansing action.

The following Examples will serve to further typify the nature of this invention without restricting the scope thereof, the scope being defined solely by the appended claims.

EXAMPLE 1

The following compositions are prepared utilizing one-half of the total composition of a basic vehicle preparation composed of the following ingredients: 10% sodium sulfosuccinate half-ester (Emcol 4300, Witco Chemical Corp.); 10% ethoxylated alkanolamine (Emcol 5130 in which the alcohol is a fatty alcohol mixture of $C_{11}$, $C_{14}$, $C_{15}$ and $C_{17}$ ethoxylated to the extent of 3 mols of ethylene oxide); 2% alkanolamide (Condensate L-90); triethanolamine lauryl sulfate (Richonol T); 5% propylene glycol; 3% borax and 10% xylene sodium sulfonate.

The ingredients of this vehicle are combined with the indicated quantities of antibacterial agents and quaternary salts and the second half of the composition is completed through the addition of water.

TABLE I

| Composition | % of Total Composition | | | | |
|---|---|---|---|---|---|
| | Halogenated Salicylanilide[1] | Halogenated Hydroxydiphenyl Ether[2] | Quat Salt[3] | Vehicle | Water |
| A | 1 | — | — | 50 | 49 |
| B | — | — | 2 | 50 | 48 |
| C | — | 0.25 | — | 50 | 49.75 |
| D | — | — | — | 50 | 50 |
| E | 1 | — | 2 | 50 | 47 |
| F | — | 0.25 | 2 | 50 | 47.75 |
| G | 1 | 0.25 | — | 50 | 48.75 |
| H | 1 | 0.25 | 2 | 50 | 46.75 |

[1] = 3,4'-tribromo salicylanilide
[2] = 2,4,4'-trichloro-2-hydroxydiphenylether
[3] = 1,3-di-[(3-mixed alkyl dimethylammonium-2-hydroxy-propoxy)-polyethoxy]-2-[(3-chloro-2-hydroxy-propoxy)-polyethoxy] propane dichloride have a total of about 12 ethoxy groups and in which the "mixed alkyl" is about 65% dodecyl, 25% tetradecyl and 10% hexadecyl (HQ8, Fine Organics, Inc.)

The antibacterial properties of these compositions can be seen from the following data on the dilutions made in sterile nutrient broth; Letheen broth serving as the subculture media with incubation for 48 hours at 37°C (media growth controls all positive).

TABLE II

| Composition | S. aureus | | E. coli | | Ps. aeruginosa | |
|---|---|---|---|---|---|---|
| | MIC | KILL | MIC | KILL | MIC | KILL |
| A | 1:800 | 1:800 | 1:10 | 1:10 | 1:10 | <1:5 |
| B | 1:3200 | 1:1600 | 1:5 | <1:5 | 1:10 | <1:5 |
| C | 1:800 | 1:200 | 1:10 | <1:5 | 1:10 | <1:5 |
| D | 1:40 | 1:40 | 1:5 | <1:5 | 1:5 | <1:5 |
| E | 1:1600 | 1:1600 | 1:5 | 1:5 | 1:5 | <1:5 |
| F | 1:200 | 1:50 | 1:6400 | <1:5 | 1:5 | <1:5 |
| G | 1:1600 | 1:800 | 1:12,500 | 1:12,500 | 1:10 | <1:5 |
| H | >1:50,000 | 1:6400 | 1:50,000 | >1:50,000 | 1:30 | 1:15 |

EXAMPLE 2

The activity of the compositions of the present invention as compared with known antibacterial surgical scrubs may be seen from the following table in which dilutions of the test material were prepared aseptically directly into Difco nutrient broth with the dilutions being incubated at 37°C for 48 hours to determine the MIC and then subcultured into a Letheen broth and incubated for 48 hours to determine kill.

TABLE III

| Organism | Composition H | | 3% Hexachlorophene | |
|---|---|---|---|---|
| | MIC | KILL | MIC | KILL |
| S. aureus | 1:50,000 | 1:6400 | 1:30 | 1:30 |
| | (−) | (−) | (−) | (−) |
| E. coli | 1:50,000 | 1:50,000 | 1:5 | 1:5 |
| | (−) | (−) | (−) | (+) |
| Ps. aeruginosa | 1:15 | 1:10 | 1:5 | 1:5 |
| | (−) | (−) | (−) | (+) |
| Salmonella choleraesuis | 1:10 | 1:5 | 1:5 | 1:5 |
| | (−) | (−) | (−) | (+) |

(−) = no growth
(+) = growth

EXAMPLE 3

A composition was prepared according to the following formulation:

| Ingredient | % Total Composition |
|---|---|
| Tribromsalan | 2 |
| HQ8 | 4 |
| 2,4,4'-trichloro-2'-hydroxydiphenyl ether | 0.5 |
| Emcol 5130 (alkanolamine condensate) | 10 |
| Emcol 4300 (sodium sulfosuccinate monoester) | 40 |
| Richonol T (triethanolamine lauryl sulfate) | 20 |
| Propylene glycol | 5 |
| Borax | 3 |
| Xylene sodium sulfonate | 5 |
| Sodium hydroxide | 3.5 |
| Water | 7 |
| Total | 100.0 |

The pH of the aforegoing composition is 9.3 and when diluted as a 10% solution, 9.1. The material has an irritation index of 1.5 when tested on skin according to the method of Draize, "Dermal Toxicity," Appraisal of the Safety of Chemicals in Foods, Drugs and Cosmetics, Staff of Division of Pharmacology, FDA, Dept. of HEW, page 47. The material is thus only mildly irritating, less so than commercial hand soap. When tested for eye irritation according to the Draize technique, loc. cit., page 46, a very low score of irritation for unwashed eye and no irritation for washed eye was observed. No damage, including damage to the brain, was observed upon dermal application daily over a period of 30 days to rats.

EXAMPLE 4

The following ingredients are combined to form a skin lotion:

| | |
|---|---|
| Stearic acid | 2.3% |
| Carboxy vinyl polymer | Ca 4% |
| Liquid lanolin, oil soluble, dewaxed, liquid fraction of cosmetic grade | 5% |
| Triethanolamine | 1% |
| Ethyl alcohol | 7% |
| Trichlorocarbanilide | 0.2% |
| 2,4,4'-trichloro-2'-hydroxydiphenyl ether | 0.1% |
| HQ8 | 0.2% |

The foregoing ingredients, to which may be added coloring agents and perfumes, are thoroughly blended.

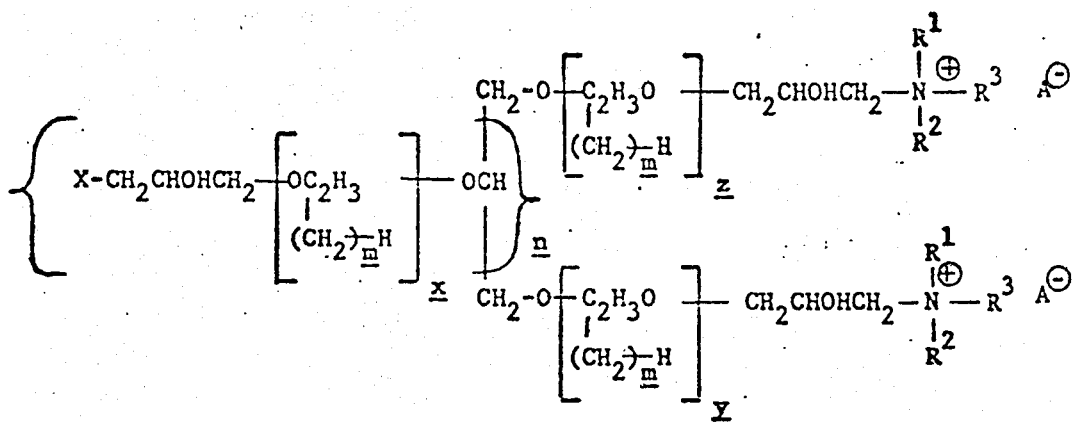

EXAMPLE 5

Following the procedure of Example 1, the following antibacterial compositions are formed:

TABLE IV

| Composition | % of Total Composition | | | | |
|---|---|---|---|---|---|
| | Component A[1] | Component B[2] | Quat Salt[3] | Vehicle | Water |
| I | 1 | 0.25 | 2 | 50 | 46.75 |
| J | 1 | 0.25 | 2 | 50 | 46.75 |

[1] Component A for composition I is 2',3,4',5-tetrabromo salicylanide. Component A for composition J is 3,4',5-tribromo salicylanide.
[2] Component B for composition I is 2,4,4'-trichloro-2-hydroxydiphenylether. Component B for composition J is 3,3',5,5'-tetrabromo-2,2'-biphenyldiol.
[3] Same as Quat Salt of Table I.

What is claimed is:

1. A topical antibacterial composition comprising an aqueous solution or emulsion of (a) an antibacterially effective amount of from about 0.05% to about 3% by weight of a halogenated salicylanilide, carbanilide or thiocarbanilide having one or two halogen atoms selected from the group consisting of chlorine and bromine on each phenyl ring and up to one trifluoromethyl on one phenyl ring; (b) an antibacterially effective amount of from about 0.025% to about 1% by weight of a halogenated 2-hydroxydiphenyl ether having one or two halogen atoms selected from the group consisting of chlorine and bromine on each phenyl ring or a halogenated bisphenol of the formula

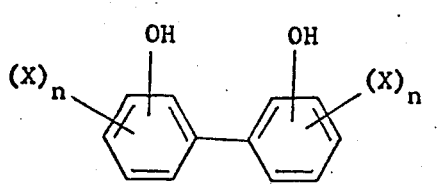

where X is chlorine or bromine and n is 1 to 4; and (c) an antibacterially effective amount of from about 0.2% to about 4% by weight of a quaternary salt of the formula:

wherein

X is chlorine or bromine; each of $R^1$ and $R^2$ is alkyl of 1 to 3 carbon atoms;

$R^3$ is alkyl, alkenyl or haloalkyl of 6 to 18 carbon atoms;

A is a physiological acceptable monovalent anion;

each of $x$, $y$ and $z$, independent of the other, has a value of from 1 to 10;

the sum of $x$, $y$ and $z$ is 9 to 15;

$m$ has a value of 0 or 1; and $n$ has a value of from 1 to 4.

2. The composition according to claim 1, wherein in said quaternary salt, X is chlorine; $R^1$ and $R^2$ are each methyl; $R^3$ is at least one alkyl group of from 12 to 16 carbon atoms; $A^-$ is the chloride anion; $m$ is 0 and $n$ is 1.

3. The composition according to claim 2, wherein the sum of $x$, $y$ and $z$ is about 12.

4. The composition according to claim 1, wherein said halogenated salicylanilide, carbanilide or thiocarbanilide is selected from the group consisting of 3,4',5-tribromo salicylanilide, 3,5-dibromo salicylanilide, 4',5-dibromo salicylanilide, 5-chloro-2',4'-dibromo salicylanilide, 3,4',5-trichloro salicylonilide, 4'-chloro-5-bromo salicylanilide, 2',3,4',5-tetrabromo salicylanilide, 3,4,4'-trichloro carbanilide, and 3-trifluoromethyl-4,4'-dichloro carbanilide.

5. The composition according to claim 4 wherein said halogenated salicylanilide is 3,4',5-tribromo salicylanilide or 2',3,4',5-tetrabromosalicylanilide; said halogenated 2-hydroxydiphenyl ether is 2',4,4'-trichloro-2-hydroxydiphenyl ether; and in said quaternary salt, X is chloro; $R^1$ and $R^2$ are each methyl;

$R^3$ is mixed alkyl of 65% dodecyl, 25% tetradecyl and 10% hexadecyl $A^-$ is the chloride anion; $m$ is 0; $n$ is 1, and the sum of $x$, $y$ and $z$ is about 12.

6. The composition according to claim 5 wherein the pH of a fivefold aqueous dilution of the composition is from about neutrality to 9.5.

7. The composition according to claim 1, wherein in said halogenated bisphenol $n$ is 1 or 2.

8. The composition according to claim 1, wherein said halogenated 2-hydroxydiphenyl ether is 2,4,4'-trichloro-2'-hydroxydiphenyl ether or 4,4'-dichloro-2'-hydroxydiphenyl ether.

* * * * *